United States Patent [19]

Finkel et al.

[11] Patent Number: 5,372,805
[45] Date of Patent: Dec. 13, 1994

[54] COSMETIC SUNSCREEN

[75] Inventors: Peter Finkel; Eckart Voss, both of Leverkusen, Germany

[73] Assignee: Bayer Aktiengesellschaft, Leverkusen, Germany

[21] Appl. No.: 76,297

[22] Filed: Jun. 11, 1993

[30] Foreign Application Priority Data

Jul. 16, 1992 [DE] Germany ............................. 4223464

[51] Int. Cl.⁵ ....................... A61K 7/42; A61K 7/44; A61K 9/107; A61K 31/44
[52] U.S. Cl. ....................................... 424/59; 424/60; 514/284; 514/938
[58] Field of Search ................................... 424/59, 60

[56] References Cited

U.S. PATENT DOCUMENTS

| | | | |
|---|---|---|---|
| 4,707,354 | 11/1987 | Garlen | 424/47 |
| 4,894,222 | 1/1990 | Matravers | 424/59 |
| 4,940,574 | 7/1990 | Kaplan | 424/59 |
| 5,102,654 | 4/1992 | Castrogiovanni et al. | 424/61 |

FOREIGN PATENT DOCUMENTS

| | | | |
|---|---|---|---|
| 343444 | 5/1989 | European Pat. Off. | 424/59 |
| 2184356 | 6/1987 | United Kingdom | 424/59 |

Primary Examiner—Dale R. Ore
Attorney, Agent, or Firm—Sprung Horn Kramer & Woods

[57] ABSTRACT

The present invention relates to a new cosmetic sunscreen in emulsion form for external application, based on absorbent and reflecting substances in combination with a new radical scavenger system, and to a process for its preparation.

8 Claims, No Drawings

COSMETIC SUNSCREEN

The present invention relates to a new cosmetic sunscreen in emulsion form for external application, based on absorbent and reflecting substances in combination with a new radical scavenger system, and to a process for its preparation.

To reduce the UV rays responsible for skin ageing and for skin damage, cosmetic sunscreens customarily contain UV A and/or UV B filters. However, the use of pigments, in particular titanium dioxide pigments, as UV-reflecting active ingredients is also known.

Vitamin E and its derivatives are frequently employed in cosmetics as a radical scavenger active ingredient. Its action is based on the antioxidant action in and on the skin (H. Möller et al. Parfümerie und Kosmetik, 68, 11, 688 (1987).

The known cosmetic sunscreens are characterised by a number of disadvantages.

The permitted UV filters are customarily only effective in the UV B range. Only one class of substance, the dibenzoylmethane derivatives, absorbs in the entire UV A range. The two permitted UV filters from this class, however, have an allergenic potential above that of the other UV filters.

Products which contain pigments as active ingredients have a relatively small allergic risk, but on account of the strong reflection of light and the high solid content (make-up effect) lead to a low user acceptance. In the modern pigment variants, the titanium dioxide micropigments, the cosmetic disadvantage is clearly diminished because of the particularly small particle size. Accompanying the small particle size, however, there is also a loss of effectiveness in the UV A range.

The function of customary vitamin E derivatives as radical scavengers in cosmetic sunscreens is limited by the inadequate and/or inhomogeneous distribution in the epidermis. Thus even in the sensitive basal layer of the epidermis, only relatively small active ingredient levels are normally attainable, and even using the liposomes frequently employed today as vehicles, no great improvement in this respect is attained.

A new cosmetic sunscreen in emulsion form has now been found, which apart from the customary bases and auxiliaries contains a combination of at least one UV filter, in particular a UV B filter and micronised, stabilised and essentially transparent zinc oxide has a UV A filter as well as a combination of vitamin E or its derivatives and 2-(dihydroxyethyl)-2-hydroxy-6,10,14-trimethyl-pentadecane. The latter compound is known as a hair care and skin care agent (G. Erkmann et al.; Seifen, Öle, Fette, Wachse 117, 10, 379 (1991). Thus, this compound is employed to maintain the moistness of the hair, to protect the hair from mechanical damage, to promote the penetration of panthenol and amino acids into the hair shaft to impart shine to dull and damaged hair and to increase the moisture-retaining ability of the skin and to keep the latter smooth and supple.

Until now, nothing has been disclosed about the use of 2-(dihydroxyethyl)-2-hydroxy-6,10,14-trimethyl-pentadecane together with vitamin E and its derivatives and, in particular, a depot effect accompanying it. This compound causes increased penetration and/or diffusion of vitamin E and its derivatives into the or in the skin respectively.

It has furthermore been found that the new sunscreens according to the invention consisting of the effective constituents such as UV A and UV B filters, vitamin E and/or its derivatives, (2-dihydroxyethyl)-2-hydroxy-6,10,14-trimethyl-pentadecane and optionally one and/or more bases or auxiliaries are obtained when the components are predispersed and stirred with one another by the customary methods and then optionally homogenised. The entire preparation is preferably carried out in an evacuated apparatus to avoid the inclusion of air.

The invention generally also relates to the new use of (2-dihydroxyethyl)-2-hydroxy-6,10,14-trimethyl-pentadecane to increase the penetration and/or diffusion of vitamin E and its derivatives into the or in the skin, in particular in cosmetic sunscreens.

Surprisingly, the sunscreen according to the invention shows none of the disadvantages described above in comparison with the sunscreen formulations known from the prior art.

For protection from UV B radiation, the recipes according to the invention contain one or more of the customarily used UV B filters, in particular one or more of the permitted UV B filters of the EC positive list. These have been published in the "Fourteenth Directive 92/8/EEC of the Commission" of 18th Feb. 1992 (for this see Official Gazette of the European Communities ABL. No. L 70/23 of 17th Mar. 1992).

The protection from UV A radiation is achieved by means of micronised and stabilised zinc oxide. In contrast to titanium dioxide, this zinc oxide has a distinctly greater transparency. This also means a substantially higher user acceptance.

In order to optimise the use of vitamin E and its derivatives, various experiments to improve the penetration and diffusion of the substance in the epidermis were carried out. It was particularly surprising that a combination of vitamin E derivatives with (2-dihydroxyethyl)-2-hydroxy-6,10,14-trimethyl-pentadecane leads to a completely homogeneous distribution of the vitamin E derivatives in the entire area of the epidermis. This is the prerequisite for optimum use of a radical scavenger system in light-exposed skin.

It was furthermore possible to show that the sunscreen according to the invention leads to a depot of vitamin derivatives, in particular vitamin E acetates, in the skin, particularly in the lower areas of the epidermis, which are important for ageing processes. This is an ideal prerequisite for the preparation of the active compound. The cosmetic sunscreen according to the invention is thus a highly effective system for protection from acute and chronic light damage of the skin and provides outstanding cosmetic properties.

Preferably, according to the invention the customary vitamin E derivatives are employed, and the vitamin E esters may be mentioned as particularly preferred. Vitamin E linoleate and vitamin E acetate or mixtures thereof are very particularly preferably used.

A new cosmetic sunscreen is preferred which contains the active constituents in the following composition:

0.1 to 20% of one or more UV B filters,
0.5 to 20% of a micronised, transparent and stabilised zinc oxide,
0.1 to 5% of vitamin E acetate,
0.1 to 5% of 2-(dihydroxyethyl)-2-hydroxy-6,10,14-trimethyl-pentadecane.

The cosmetic sunscreen according to the invention furthermore contains one or more of the following substances as bases and/or auxiliaries:

Antioxidants, solvents, mineral, animal or vegetable oils or waxes, fatty acids, fatty alcohols, fatty acid esters, fatty alcohol ethers, ethoxylated fatty alcohols, lanolin or lanolin derivatives, silicone oils, emulsifiers, thickeners, humectants, colorants, buffer substances, preservatives and perfume oils.

The sunscreen according to the invention particularly preferably contains
 0.5 to 10% of one or more UV B filters,
 1 to 10% of a micronised, transparent and stabilised zinc oxide,
 0.2 to 4% of vitamin E acetate,
 0.2 to 4% of 2-(dihydroxyethyl)-2-hydroxy-6,10,14-trimethyl-pentadecane,
and one or more of the abovementioned bases and/or auxiliaries.

A sunscreen formulation which is very particularly preferred is one which contains
 2 to 6% of one or more UV B filters,
 3 to 6% of a micronised, transparent and stabilised zinc oxide,
 0.5 to 2% of vitamin E acetate,
 0.5 to 2% of 2-(dihydroxyethyl)-2-hydroxy-6,10,14-trimethyl-pentadecane,
and one or more of the abovementioned bases and/or auxiliaries.

Suitable UV B filters are preferably all the compounds mentioned in the EC positive list. This includes benzylidenecamphor compounds, p-aminobenzoic acid and its derivatives, cinnamates, benzoxazole derivatives, benzophenone derivatives and benzotriazole derivatives.

Preferably, the following UV B filters are employed for the formulation of the sunscreen according to the invention:

N-Propoxylated ethyl 4-aminobenzoate (mixture of isomers),
Ethoxilated ethyl 4-aminobenzoate,
Glyceryl 4-aminobenzoate,
2-Ethylhexyl 4-dimethylaminobenzoate,
2-Ethylhexyl salicylate,
Isopentyl 4-methoxicinnamate (mixture of isomers),
2-Ethylhexyl 4-methoxycinnamate,
2-Hydroxy-4-methoxy-4'-methyl-benzophenone (mexenone (INN)],
2-Hydroxy-4-methoxybenzophenone-5-sulphonic acid and sodium salt (sulisobenzone and sodium salt),
α-(2-Oxoborn-3-ylidene-toluene)-4-sulphonic acid and its salts,
3-(4'-Methylbenzylidene)-d,l-camphor,
3-Benzylidenecamphor,
4-Isopropyl-dibenzoylmethane,
4-Isopropylbenzyl salicylate
1-(4-tert.Butylphenyl)-3-(4-methoxyphenyl)propane-1,3-dione,
2,4,6-Trianilino-(p-carbo-2'-ethylhexyl-1'-oxi)-1,3,5-triazine.

The following compounds are particularly preferably employed as UV B filters:

2-Ethoxyhexyl p-(dimethylamino)-benzoate;
2-Ethylhexyl p-methoxycinnamate;
3-(4'-methylbenzylidene)-d,l-camphor;
2-Hydroxy-5-methoxybenzophenone;
2-Hadroxy-4-methoxybenzophenone-5-sulphonic acid;
2-Phenylbenzimidazole-5-sulphonic acid.

Suitable UV A filters are preferably micronised zinc oxide grades having a primary particle size of 5 to 100 μm, preferably 10 to 100 μm, particularly preferably 10 to 50 μm.

Material coated on micronised zinc oxide and predispersions thereof in oil components are particularly highly suitable for processing for the cosmetic sunscreen according to the invention.

Apart from the abovementioned active compound combination, the cosmetic sunscreen according to the invention contains bases and auxiliaries customarily employed in cosmetic agents, in particular stabilisers and antioxidants such as butylhydroxyanisole, butylhydroxytoluene, EDTA, and salts such as magnesium sulphate in amounts from 0.02 to 5%, inter alia.

The bases and auxiliaries additionally include solvents customary in cosmetics such as water to 80%, monoalcohols, lower polyalcohols having 1 to 6 carbon atoms or mixtures thereof, furthermore fatty material, such as mineral, animal or vegetable oils such as paraffin oil or waxes such as microwax, fatty acids, fatty alcohols, fatty acid esters such as cetylstearyl isononanoate and isopropyl palmitate, fatty alcohol ethers, ethoxylated fatty alcohols, lanolin and derivatives, silicone oils in amounts from 0.5 to 50%, preferably 0.5 to 30%, particularly preferably in amounts from 5 to 30%.

The cosmetic sunscreen according to the invention optionally contains emulsifiers in amounts from 0.1 to 20%, preferably in amounts from 0.2 to 10%, these being nonionic, anionic, cationic or amphoteric compounds, for example sterols, polyol fatty acid esters and polyol fatty alcohol ethers, alkali metal and triethanolamine salts of fatty acids, sodium cetylstearyl sulphate, tetracyl-ammonium halides and phospholipids. Examples of these are glycerol sorbitol fatty acid esters, polyoxyethylene fatty acid esters and alkyltetraglycol ether o-phosphoric acid esters.

Thickeners can also be employed in the sunscreens according to the invention. These include polyacrylic acid derivatives, cellulose derivatives, bentonites, xanthan derivatives, alginates, guar gum and locust bean gum. Preferably, polyacrylamide or zinc stearate is employed in concentrations from 0.02 to 5%, preferably in amounts from 0.1 to 2%.

The sunscreen formulation according to the invention can contain further substances which are customary in cosmetic compositions such as humectants, colorants, buffer substances, preservatives and perfume oils. These include humectants in amounts from 0.5 to 15%.

Humectants which may be mentioned by way of example are:
 Lower polyalcohols such as glycerol, propylene glycol, butylene glycol, sorbitol, in addition 2-pyrrolidone-5carboxylic acid and its sodium salt, lactic acid and its salts, urea, proteins and protein derivatives such as collagen, and in addition hyaluronic acid, inter alia.

Dyes to be added to the sunscreens according to the invention which may be mentioned by way of example are:
 dye C.I. 16255, dye C.I. 61570, dye C.I. 42051, dye C.I. 15985, dye C.I. 77492.

The amount thereof is about 0.01 to 5.0% of the total formulation amount.

Suitable preservatives are preferably:

2,4-Hexadienoic acid (sorbic acid and its salts)
4-Hydroxybenzoic acid, its salts and esters,
3-Acetyl-6-methyl-2,4(3H)-pyrandione (dehydracetic acid) and its salts,
1,1-Methylene-bis-[3-(1-hydroxy-methyl-2,4-diocimidazolidin-5-yl)urea],
Imidazolidinylurea,
2-Phenoxy-ethanol and
Benzyl alcohol.

Like the amounts of buffer substances and perfume oils to be optionally added, the amount thereof is also 0.01 to 5% of the total formulation amount of the sunscreen according to the invention.

The cosmetic composition according to the invention is present as an emulsion (cream or milk). It is prepared, inter alia, by mixing and stirring the components, if appropriate with subsequent homogenisation and if appropriate in an evacuated apparatus.

All percentages in the present test relate to percentages by weight, if not stated otherwise.

The invention is illustrated in greater detail in the following by the examples, without it being intended that these have a restrictive character.

EXAMPLE 1

Water-in-Oil Emulsion (Sun Cream)

|      |                                                   |                    | (Data in g) |
|------|---------------------------------------------------|--------------------|-------------|
| I.   | Glycerol sorbitan fatty acid ester                | (emulsifier)       | 8.0         |
|      | Cetylstearyl isononanoate                         |                    | 10.0        |
|      | Paraffin, low viscosity                           | (fat components)   | 7.0         |
|      | Microwax                                          |                    | 2.0         |
|      | Ethylhexyl p-methoxycinnamate                     | (UV B filter)      | 5.0         |
|      | Zinc stearate                                     | (gelling agent)    | 2.0         |
| II.  | Zinc oxide (micronised/stabilised)                | (UV A protection)  | 5.0         |
| III. | Vitamin E acetate                                 |                    | 1.0         |
|      | 2-(dihydroxyethyl)-2-hydroxy-6,10,14-trimethyl-pentadecane |          | 1.0         |
| IV.  | Perfume oil                                       |                    | 0.5         |
|      | Preservative                                      |                    | q.s. *      |
| V.   | Glycerol                                          | (humectants)       | 0.5         |
|      | Water to                                          |                    | 100.0       |

Preparation

The mixture I is fused at 75° C., II is dispersed in and the solution V, which is heated to the same temperature, is added with stirring. The mixture is allowed to cool to 35° C. with further stirring and homogenisation, then the mixture of III and IV is added, made up with water to 100 g and allowed to cool to room temperature with further stirring. The entire preparation is carried out in an evacuated apparatus to avoid the inclusion of air.

EXAMPLE 2

Water-in-Oil Emulsion (Sun Milk)

|      |                                     |                  | (Data in g) |
|------|-------------------------------------|------------------|-------------|
| I.   | Polyethylene fatty acid ester       | (emulsifier)     | 6.0         |
|      | Glycerol sorbitan fatty acid ester  | (emulsifier)     | 2.0         |
|      | Microwax                            |                  | 1.0         |
|      | Paraffin, low viscosity             | (fat components) | 13.0        |
|      | Isopropyl palmitate                 |                  | 7.0         |
|      | Ethylhexyl p-methoxycinnamate       | (UV B filter)    | 5.0         |
| II.  | Zinc oxide (micronised/stabilised)  |                  | 5.0         |
| III. | Vitamin E acetate                   |                  | 1.0         |
|      | 2-(dihydroxyethyl)-2-hydroxy-6,10,14-trimethyl-pentadecane |  | 1.0 |
| IV.  | Perfume oil                         |                  | 1.0         |
|      | Preservative                        |                  | q.s. *      |
| V.   | Glycerol                            | (humectant)      | 4.0         |
|      | Magnesium sulphate                  | (stabiliser)     | 0.7         |
|      | Water to                            |                  | 100.0       |

The W/O emulsion (skin care composition) is prepared in analogy to the data of Example 1.

EXAMPLE 3

Oil-in-Water Emulsion (Sun Milk)

|      |                                                   |                   | (Data in g) |
|------|---------------------------------------------------|-------------------|-------------|
| I.   | Alkyltetraglycol ether o-phosphoric acid ester    | (emulsifier)      | 2.0         |
|      | Cetylstearyl alcohol                              |                   | 2.0         |
|      | Paraffin, low viscosity                           | (fat components)  | 5.0         |
|      | Isopropyl palmitate                               |                   | 5.0         |
|      | Ethylhexyl p-methoxycinnamate                     | (UV B filter)     | 5.0         |
| II.  | Polyacrylamide                                    | (thickener)       | 0.7         |
|      | Zinc oxide (micronised/stabilised)                |                   | 5.0         |
| III. | Vitamin E acetate                                 |                   | 1.0         |
|      | 2-(dihydroxyethyl)-2-hydroxy-6,10,14-trimethyl-pentadecane |           | 1.0         |
| IV.  | Perfume oil                                       |                   | 0.5         |
|      | Preservative                                      |                   | q.s. *      |
| V.   | Glycerol                                          | (humectant)       | 3.0         |
|      | Water to                                          |                   | 100.0       |

Preparation

The mixture I is fused at 75° C., II is dispersed in and the solution V, which is heated to the same temperature, is added. The mixture is allowed to cool to 35° C. with further stirring and homogenisation, then the mixture of III and IV is added, and the mixture is made up to 100 g with water and allowed to cool to room temperature with further stirring. The entire preparation is carried out in an evacuated apparatus in order to avoid the inclusion of air.

EXAMPLE 4

Water-in-Oil Emulsion (Sun Cream)

|      |                                              | Data in g |
|------|----------------------------------------------|-----------|
| I.   | Polyethylene glycol-l-glycerol-sorbitan isostearate | 10.0 |
|      | Beeswax                                      | 3.0       |
|      | Lanolin                                      | 3.0       |
|      | Caprylic/caproic acid triglyceride           | 6.0       |
|      | Perhydrosqualene                             | 6.0       |
|      | Wheat germ oil                               | 3.0       |
|      | Ethylhexyl p-methoxycinnamate                | 5.0       |
| II.  | Zinc oxide (micronised/stabilised)           | 5.0       |

-continued

|      |                                                                        | Data (in g) |
|------|------------------------------------------------------------------------|-------------|
| III. | Vitamin E acetate                                                       | 1.0         |
|      | 2-(dihydroxyethyl)-2-hydroxy-6,10,14-trimethyl-pentadecane              | 1.0         |
|      | Ascorbyl palmitate                                                      | 0.1         |
| IV.  | Perfume oil                                                             | q.s.        |
| V.   | Glycerol                                                                | 2.0         |
|      | Preservative                                                            | q.s.        |
|      | Magnesium sulphate                                                      | 0.7         |
|      | Water to                                                                | 100.0       |

Preparation

The mixture I is fused at 75° C., II is dispersed in and the solution V, which is heated to the same temperature, is added with stirring. The mixture is allowed to cool to 35° C. with further stirring and homogenisation, then the mixture of III and the perfume oil IV is added, and the mixture is made up to 100 g with water and allowed to cool to room temperature with further stirring. The entire preparation is carried out in an evacuated apparatus in order to avoid the inclusion of air.

EXAMPLE 5

Water-in-Oil Emulsion (Sun Milk)

|      |                                                                           | Data (in g) |
|------|---------------------------------------------------------------------------|-------------|
| I.   | Polyethylene glycol-1,5-polyoxyethylene-2,5-glycerol-sorbitan hydroxystearate | 6.0         |
|      | Cyclomethicone                                                             | 6.0         |
|      | Paraffin, low viscosity                                                    | 6.0         |
|      | Ethylhexyl P-methoxycinnamate                                              | 3.0         |
| II.  | Zinc oxide (micronised/stabilised)                                         | 5.0         |
| III. | Vitamin E acetate                                                          | 1.0         |
|      | 2-(dihydroxyethyl)-2-hydroxy-6,10,14-trimethyl-pentadecane                 | 1.0         |
| IV.  | Perfume oil                                                                | q.s.        |
| V.   | Polyethylene glycol-sorbitol                                               | 4.0         |
|      | Magnesium sulphate                                                         | 0.7         |
|      | Preservative                                                               | q.s.        |
|      | Water to                                                                   | 100.0       |

The water-in-oil emulsion (sun milk) according to Example 5 is prepared in analogy to the data of Example 4.

It will be understood that the specification and examples are illustrative but not limitative of the present invention and that other embodiments within the spirit and scope of the invention will suggest themselves to those skilled in the art.

What is claimed is:

1. In a cosmetic sunscreen composition comprising an effective sunscreening amount of a combination of effective amounts of (a) at least one UV A or B filter, (b) micronized, stabilized and essentially transparent zinc oxide, and (c) at least one of vitamin E and a derivative thereof, wherein the improvement comprises an effective amount of (d) 2-(dihydroxyethyl)-2-hydroxy-6,10,14-trimethyl-pentadecane to increase protection from acute and chronic light damage of the skin.

2. The composition according to claim 1, wherein (c) comprises at least one of vitamin E linoleate and vitamin E acetate.

3. The composition according to claim 1, comprising the components in the following approximate percentages by weight:
   (a) 0.1 to 20% of at least one UV B filter,
   (b) 0.5 to 20%,
   (c) 0.1 to 5% and
   (d) 0.1 to 5%.

4. The composition according to claim 1, comprising the components in the following approximate percentages by weight:
   (a) 0.1 to 20% of at least one UV B filter,
   (b) 0.5 to 20%,
   (c) 0.2 to 4% of vitamin E acetate and
   (d) 0.1 to 5%.

5. The composition according to claim 1, comprising the components in the following approximate percentages by weight:
   (a) 0.5 to 10% of one or more UV B filters,
   (b) 1 to 10% of a micronized, essentially transparent and stabilized zinc oxide,
   (c) 0.2 to 4% of vitamin E acetate and
   (d) 0.2 to 4% of 2-(dihydroxyethyl)-2-hydroxy-6,10,14-trimethyl-pentadecane.

6. The composition according to claim 1, wherein the composition is an oil-in-water or water-in-oil emulsion in milk or cream form.

7. The composition according to claim 1 additionally comprising at least one cosmetic auxiliary agent selected from the group consisting of an antioxidant, solvent, mineral oil, mineral wax, animal oil, animal wax, vegetable oil, vegetable wax, fatty acid, fatty alcohol, fatty acid ester, fatty alcohol ether, ethoxylated fatty alcohol, lanolin, a lanolin derivative, silicone oil, emulsifier, thickener, humectant, colorant, buffer, preservative and perfume oil.

8. In an improved sunscreening method comprising applying to the skin an effective sunscreening amount of the composition as defined in claim 1.

* * * * *